United States Patent [19]
Christoudias

[11] Patent Number: 5,688,230
[45] Date of Patent: Nov. 18, 1997

[54] ENDODISSECTOR

[75] Inventor: George Christoudias, New Milford, N.J.

[73] Assignee: Surgical Inventions & Innovations, Inc., New Milford, N.J.

[21] Appl. No.: 417,242

[22] Filed: Apr. 5, 1995

[51] Int. Cl.⁶ ................................................ A61M 35/00
[52] U.S. Cl. ................................................ 604/1; 606/151
[58] Field of Search ................................ 604/1–15; 606/1, 606/151, 205–211; 128/898

[56] References Cited

U.S. PATENT DOCUMENTS

| | | |
|---|---|---|
| 3,324,855 | 6/1967 | Heimlich ................................... 604/3 |
| 3,938,898 | 2/1976 | Reitknecht ............................... 604/2 |

FOREIGN PATENT DOCUMENTS

| | | | |
|---|---|---|---|
| 0759873 | 2/1934 | France | ................................... 604/2 |
| 0387242 | 2/1933 | United Kingdom | .................. 604/1 |
| 0013059 | 10/1960 | United Kingdom | .................. 604/1 |

*Primary Examiner*—Glenn Dawson
*Attorney, Agent, or Firm*—Richard A. Joel, Esq.

[57] ABSTRACT

The Christoudias endodissector is utilized for dissecting, wiping, sponging or cleaning tissues during endoscopic surgery. The instrument includes a mesh gauze body at one end which is held securely and housed in a recess on the head portion of the instrument by teeth on a fixed and a pivotal jaw. The lower part of the head portion is mounted within a resiliently backed cylindrical locking sheath. The lower head portion becomes an elongated main stem which is mounted within a handle sheath at the other end of the instrument. A locking pin on the stem engages a groove on the locking sheath to maintain the jaws in position. Alternate embodiments involve a mushroom dissector and a cocoon dissector named after the configuration of the gauze body. The invention also includes the method of making and using the Christoudias endodissector.

6 Claims, 9 Drawing Sheets

ENDODISSECTOR

BACKGROUND OF THE INVENTION

The number of laparoscopic procedures is steadily increasing as more and more surgeons are becoming accustomed to the endoscopic modality of operating. Indeed, numerous new instruments and devices have been introduced and are being used to facilitate the performance of endoscopic operations. With the broadening spectrum of procedures being performed, there is increased demand for more specialized instruments. In response to this demand, the present invention discloses a new specialized instrument for dissecting, wiping, sponging or cleaning the tissues during endoscopic surgery, known as the Christoudias endodissector.

In the prior art, an instrument with similar functions has been used extensively in conventional surgery and is known as a "peanut" and/or "dissector". This "peanut" or "dissector" is comprised of mesh gauze shaped in the form of a ball which is marketed as "weck-sorb" by "pilling weck".

This ball shaped mesh gauze is grasped firmly by the end portions or tip of any commonly used surgical clamp such as a "Kelly Clamp", "tonsil clamp", "hemostat", etc. and by manipulating the clamp, the ball shaped mesh gauze is used for dissection, cleaning, sponging and or wiping the target tissues. While this "dissector" is suitable for conventional surgery, it cannot be used in laparoscopic surgery since there is a limit on the dimensions of the instrument with the mesh gauze ball that can pass through a standard endoscopic port. This precludes the use of conventional surgical instruments for these purposes. On the other hand, the use of the laparoscopic graspers currently available for these functions are both difficult to use and often dangerous. The graspers are difficult to use because the grasping surface is neither suitable nor strong enough to close firmly on the gauze ball thus leaving the jaws partially open and therefore generally too bulky to go through the port. If the laparoscopic grasper with the gauze ball did go through the port, it is possible that due to the imperfect grasp, the mesh gauze ball could escape from the instrument and become lost in the abdomen. Endless amounts of time would then have to be consumed to find and retrieve the gauze mesh ball to avoid life threatening consequences.

A disposable laparoscopic "peanut" manufactured by U.S. Surgical under the name of Endopeanut consists of a long stem having a piece of mesh gauze rolled and fixed in place over one end. The functioning gauze end is cylindrical and is lacking in strength and uniformity; it is not nearly as strong and easy to manipulate as the open conventional surgery "peanut" or "dissector".

The present invention is intended to fill this void by providing an endoscopic grasper specifically made to accommodate comfortably, firmly and securely a mesh gauze ball currently on the market and also by designing and proposing a method of manufacturing an alternate mesh gauze ball dissector to be used with this instrument. This invention also proposes an alternate instrument that will firmly hold an alternate mesh gauze body that can be securely affixed onto the instrument.

SUMMARY OF THE INVENTION

The present invention comprises a new and improved instrument and a method for dissecting, separating, sponging, wiping, retracting or cleaning tissues during the performance of endoscopic and/or conventional surgery.

The instrument is composed of several components which assembled comprise an elongated cylindrical instrument which can accommodate and hold firmly and securely the "peanut" or "dissector" which is currently used in conventional surgery. The Christoudias endodissector comprises a method and instrument for dissecting, wiping, sponging or cleaning tissues during endoscopic surgery. The instrument basically includes a head with the dissector extending outwardly therefrom at one end, an elongated body and a handle at the other end. The instrument includes a mesh gauze body at one end which is held securely and housed in a recess on the head end portion of the instrument by teeth on a fixed and a pivotal jaw. The lower portion of the head is mounted within a cylindrical locking sheath which is resiliently backed by a spring mounted within a handle sheath at the other end of the instrument. A locking pin on the stem engages a groove on the locking sheath to maintain the jaws in position. Alternate embodiments involve a mushroom dissector and a cocoon dissector named after the configuration of the gauze body. The invention also includes the method of making and using the Christoudias endodissector.

Accordingly, an object of this invention is invention is to provide a new and improved instrument that can house and hold firmly and securely a dissector for endoscopic surgery.

A further object of this invention is to provide a new and improved gauze mesh dissector for endoscopic surgery made of tube stretch gauze mesh in a cocoon or oval shape and a method of manufacturing and using same;

A further object of the invention is to provide an instrument that is specifically designed to accept a new and improved mushroom shaped stretch mesh gauze dissector in a firm, secure and safe manner so that it can be used in both endoscopic and conventional surgery for dissecting, separating, sponging, wiping, retracting or cleaning human tissues;

A further object of this invention is to provide a mushroom shaped gauze receptor which can securely and stretchably mount the tube stretch gauze forming a "dissector" gauze surface over the cup of the mushroom while the other end is comprised of a screw which can be accommodated firmly, safely and securely by a specifically designed instrument; and, A more specific object of this invention is to provide a new and improved method and dissector for endoscopic surgery which includes a head with a pivotal jaw to grasp a mesh body within a recess, an elongated intermediate stem having a resiliently backed locking sheath adjacent the head portion to lock the jaws in position and a handle at the opposite end coupled to the stem.

BRIEF DESCRIPTION OF THE DRAWINGS

The above and other objects of the invention will become more apparent when viewed in conjunction with the accompanying drawings wherein:

FIG. 3b shows a top view of the jaw section in FIG. 3a;

FIGS. 5, 6a, 6b, 7,8, and 9a,b show the various components of the endodissector.

FIG. 13a–f illustrates the various steps in the manufacturing of the sponge dissector of the current invention by using a cylindrical tubular stretch gauze and a straight clamp; and, FIGS. 14, 14a, 15 and 15a illustrate the manufacturing and holding of the mushroom shaped and cocoon shaped dissectors by using the corresponding frame, receptor, and manipulating handles.

DETAILED DESCRIPTION OF THE INVENTION

Referring now to the drawings, the Christoudias endodissector 10 comprises an instrument suitable for dissection, sponging, retracting, cleaning, and/or wiping tissues or organs in laparoscopic, endoscopic or conventional surgery. The instrument includes two main components. The first component, a mesh gauze dissector 11 hereinafter referred to as "dissector", comprises a stretch tube of gauze mesh 12 composed of a natural or man-made fiber, or plastic in various shapes. The second component, the "dissector transporter" 15 is the instrument that transports the "dissector" 11 to the target organ in an expeditious, safe and efficient way by firmly grasping said dissector 11 between a movable and a fixed jaw 13 and 14, respectively, and securing said jaws in a fixed position by locking mechanism 16, FIG. 1a, 1b.

Figure 1:
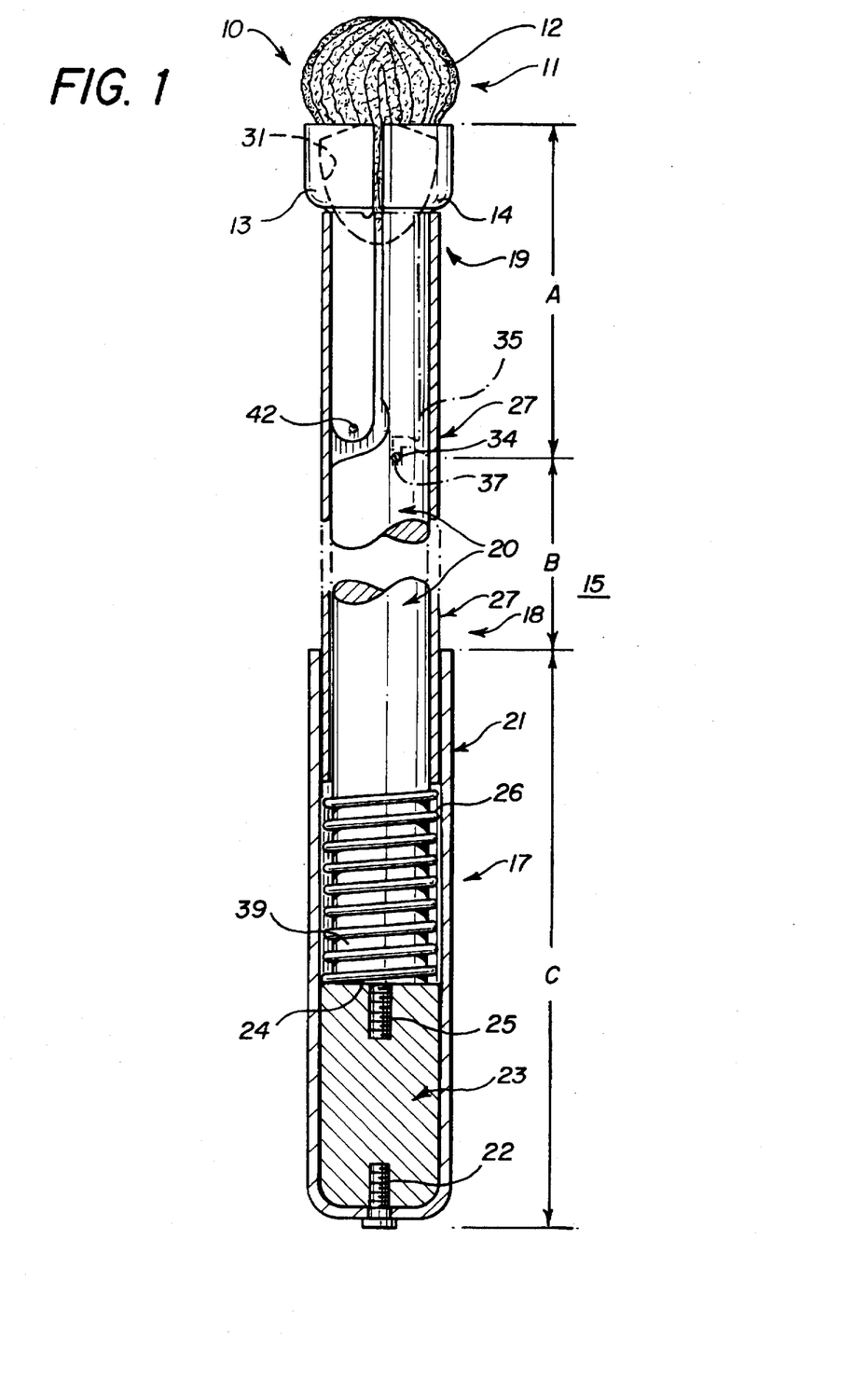
FIG. 1 represents a cut away of the Christoudias Endodissector grasper loaded with an egg shaped stretch gauze mesh dissector ready for use.

FIG. 1 illustrates in detail the different components of the dissector transporter 15, which is divided in three main parts; the handle 17, the body 18, and the head 19.

Figure 5:
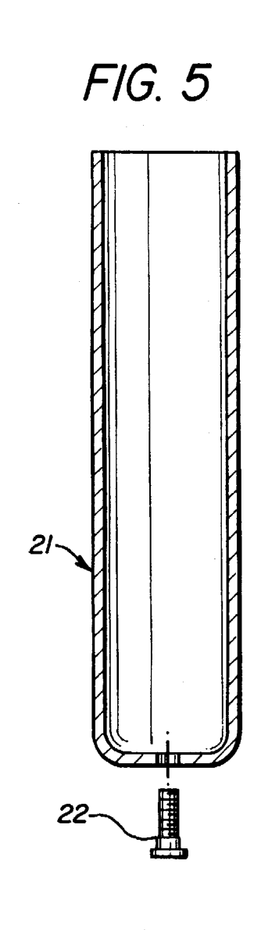
FIG. 5 shows the handle sheath and screw.
Figure 6A:
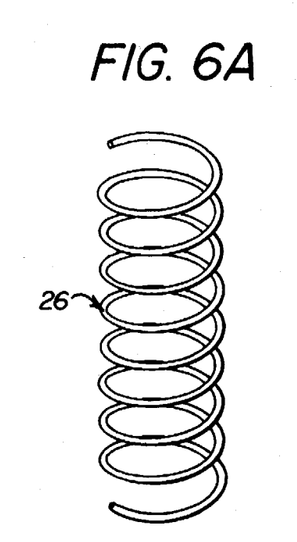
FIG. 6a shows the closing spring and FIG. 6b, the handle and spring rest.
Figure 6B:
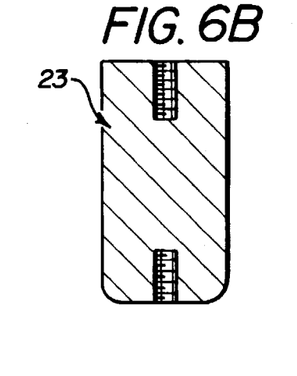

The handle 17 comprises a handle sheath 21 and screw 22, FIG. 5, and a cylindrical element 23, FIG. 6b and FIG. 1, over which the handle sheath 21 is secured by screw 22 at one end of the instrument 10. The main stem 20 comprises an elongated cylindrical element which is mounted within the handle sheath 21 and includes a connecting screw 25 which engages a threaded portion 28 of the cylindrical element 23 on its upper surface 24. A closing spring 26, FIG. 6a which applies headward force onto the external locking sheath 27, is also part of the handle 17 as is a corresponding part of the main stem 20, which extends axially within sheath 27. The spring 26 is mounted about the stem 20 with its lower portion engaging the upper surface 24 of the handle and spring rest 23. The stem 20 includes a threaded connection 25 at its lower end which joins the stem 20 to the handle 17 and spring rest 23 within the handle sheath 21 to form a unitary structure.

Figure 1A:
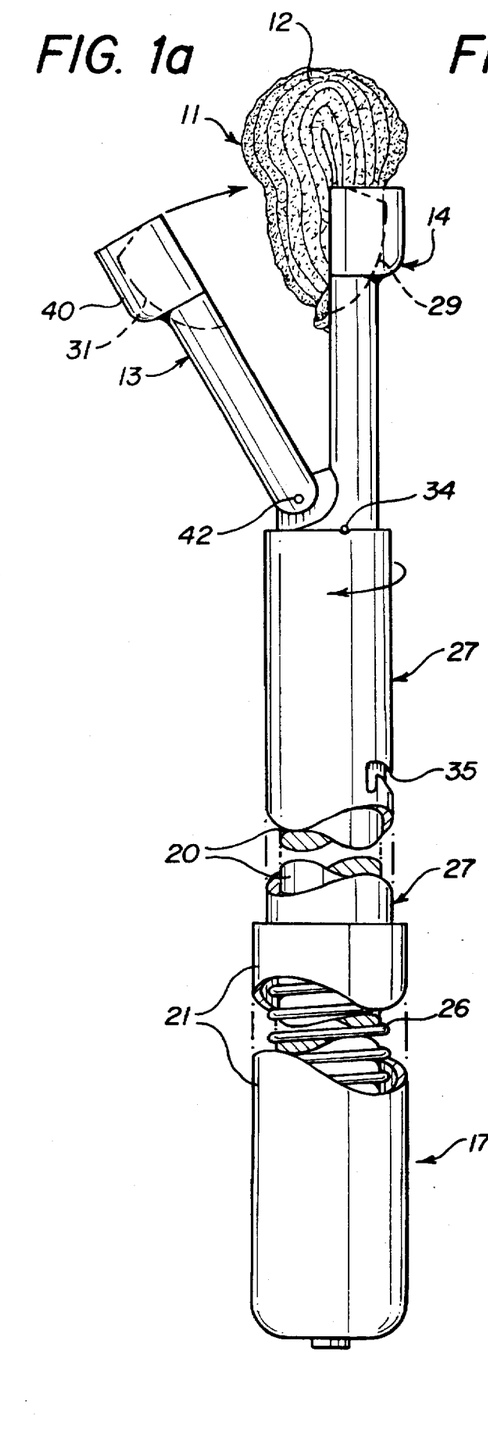
FIG. 1a shows the Christoudias endodissector with the locking sheath disengaged, the dissector gauze positioned in the fixed jaw sponge receptor space before the movable jaw is closed.
Figure 1B:
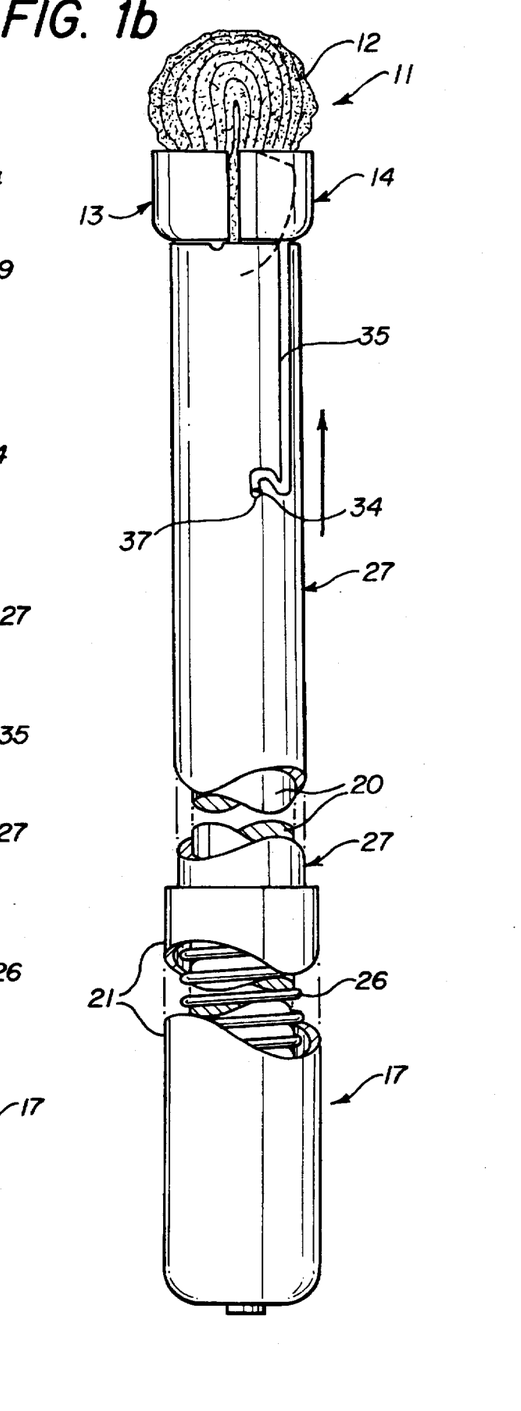
FIG. 1b shows the Christoudias endodissector with the loading sheath engaged and the movable jaw closed.

Portions of the main stem 20, and the external locking sheath 27, make up the body of the instrument, which starts at the level of the open end of the handle sheath 21 and ends at the level of the locking pin 34, FIGS. 1, 1a, 1b.

Figures 2A, 2B:
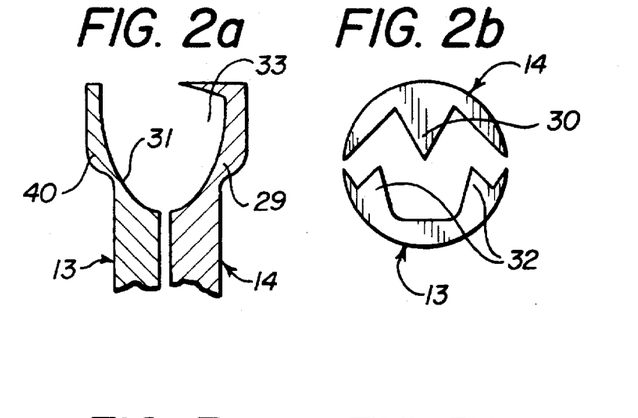
FIG. 2a is a longitudinal section through the jaw passing through the center of the instrument showing the egg shaped sponge receptor space and the fixation holding teeth of the fixed jaw.
FIG. 2b shows a face on view at the distal end of the instrument with the movable and fixed jaws and their corresponding fixation holding teeth.

In the closed or functional position, the head 19 of the dissector transporter 15, FIGS. 1, 1a, 1b is comprises a fixed jaw 14 which ends in a semicircular surface 29 with a central holding tooth 30, projecting from the periphery towards the central axis of the instrument 10, FIGS. 2a, 2b. A pivotally movable jaw 13 terminates in a semicircular surface 31 with two holding teeth 32 projecting from the periphery towards the central axis of the instrument 10. When the movable jaw 13 is in the closed position, it forms together with the fixed jaw 14, the dissector housing space 33. This is a cup shaped space 33 that will house the dissector 11, FIGS. 1 and 7. The dissector housing space 33 could also be described as eggshaped with the teeth 30, 32 dissecting the egg through its mid-point.

A part of the head 19 also includes a locking pin, 34, FIGS. 1, 1a, 1b and 7. The locking pin 34 is a 1 mm diameter pin projecting by 1 mm from the periphery of the main stem at a level at least 2 mm more towards the center than the closest point of the movable jaw 13, FIG. 7.

Figure 8:
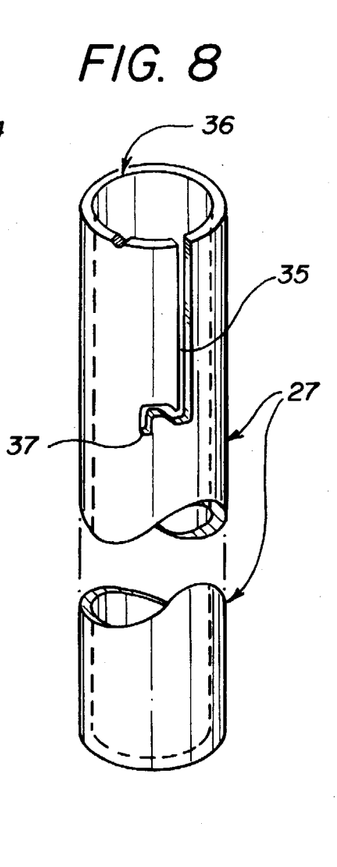
FIG. 8 shows the external locking sheath and FIGS. 9a and 9b show the jaws and teeth for holding the gauze.
Figure 9A:
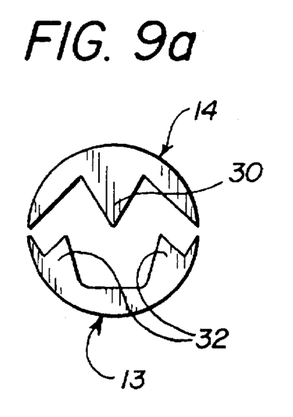
Figure 9B:
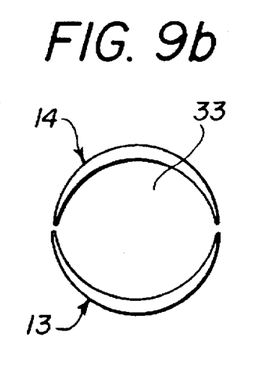
Figure 9C:
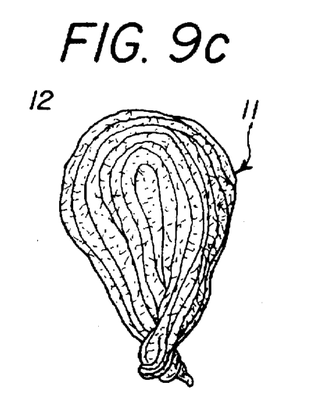
FIG. 9c shows an egg-shaped tubular gauze dissector.

The other element of the head 19 is the external locking sheath 27 which includes the elongated locking groove 35, FIGS. 1 and 8 which extends along the surface of the sheath 27 from the distal lip 36. The groove 35 extends axially along the sheath to a predetermined point and then moves back at an angle to a second point, extends perpendicular to the elongated portion to a point and then parallel to the initial axial groove 35 to a final locking point 37.

The sheath 27 is rotationally movable around the main stem 20 as well as movable along the main axis of the instrument. This allows the locking pin 34 to be guided through the locking groove 35 and locked in position at point 37 by the forward pressure of the closing spring 26, FIG. 1, which firmly and securely locks the opposing jaws 13, 14 of the grasper with the dissector 11 safely and effectively engaged for operation.

A step by step process in assembling and readying this invention will more clearly indicate its function and use.

Figure 7:
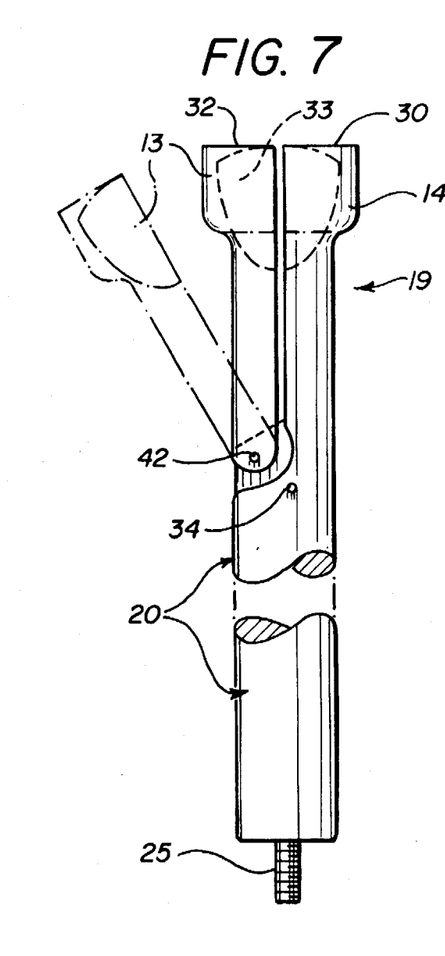
FIG. 7 shows the main stem and jaws.

The main stem 20, FIG. 7 is inserted into the locking sheath 27, FIG. 8. With the jaws 13, 14 closed, the locking sheath 27 is advanced and the locking pin 34 guided to the most distant end 37 of the locking groove 35. The distal lip 36 of the locking sheath 27, FIG. 8, rests on the outer curved portion 38 of the jaw recess 33 towards the distal end of the jaws, 13, 14. The closing spring 26, FIG. 6a, is then guided over the main stem 20 at the connecting screw end of the handle and spring rest 32, FIG. 6b is then securely and snugly screwed onto the main stem 20 via a connecting screw 25, FIGS. 1, 6b and 7. The handle sheath 21 is then secured snugly over the handle and spring rest 23 with the handle screw 22. The dissector transporter 15 is now ready for use in laparoscopic or conventional surgery.

Steps During Uses of the Christoudias Endodissector

In use, the locking sheath 27 is retracted away from the jaws 13, 14 by the appropriate rotational movement, then moved along the main axis to a position more central to the locking pin 34 and then rotated so that the locking pin 34 is engaged by the locking recess The movable jaw 13 includes an upper outwardly portion having teeth 32 on its inner surface and an elongated downwardly extending portion 41 which is pivotally connected to the main stem 20 by pivot pin 42. The jaw 13 is opened manually and the "dissector" 11 placed in the corresponding part of the fixed jaw's housing space 33. The movable jaw 13 is then brought to the closed position as shown in FIG. 1 and the external locking sheath 27 guided over it by guiding the locking pin 34 to the distant most end 37 of the locking groove 35. The dissector 11 is thus engaged in the housing space 33 and secured snugly and securely with the holding teeth 30, 32 of the opposing jaws, 13 and 14.

The jaw 13 is locked in the closed position by the locking sheath 27, which is in turn pressed headward by the closing spring 26. The endodissector 10 is now ready for introduction through an appropriate port into a body cavity and manipulated accordingly for dissection, retraction, cleaning, sponging or wiping the target organ or tissue.

When the dissector 11 is soaked with blood, debris, or other tissue, the instrument 10 is withdrawn, the sheath 27 retracted, the movable jaw 13 opened, and the gauze covered dissector 11 removed. A new dissector 11 is installed in the manner indicated and the instrument 10 used again with the steps being repeated as often as necessary.

Figure 3A:
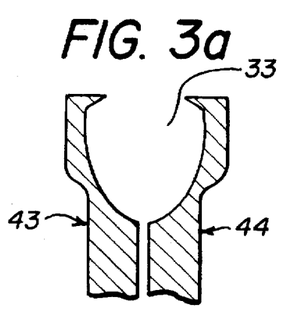
FIG. 3a shows the longitudinal section through an alternate embodiment of the jaws with a circumferential lip for fixation and holding of the cocoon dissector.
Figure 3B:
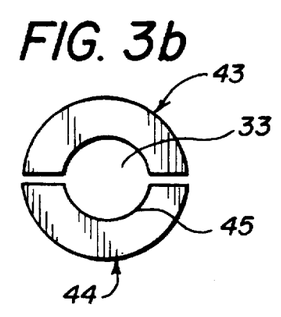
Figure 4A:
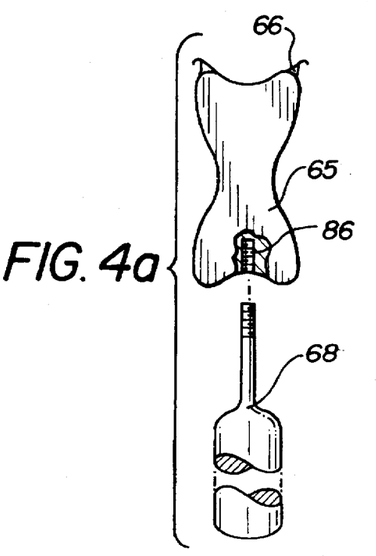
FIG. 4a shows the cocoon frame and the attaching manipulating screw and handle.
Figures 4B, 4C:
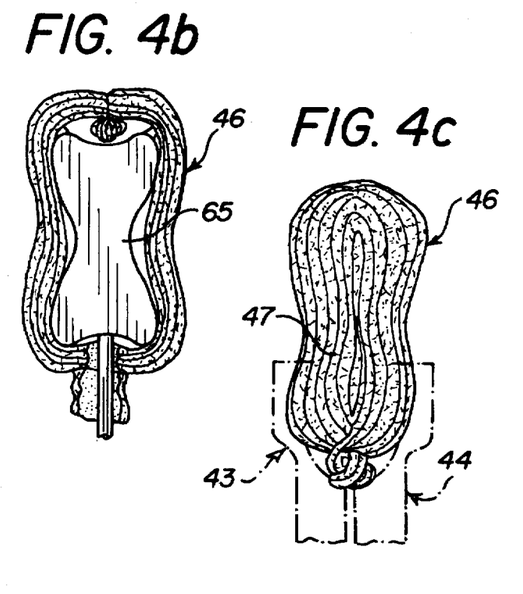
FIG. 4b shows the cocoon frame with the stabilizing screw attached and the mesh gauze applied thereover.
FIG. 4c shows the cocoon dissector completed and engaged by the endodissector grasper.

An alternate embodiment of the jaws 43, 44 of the instrument 10, FIG. 3, calls for a circular projection at the end of each jaw 43, 44 projecting transversely from the periphery towards the central axis of the instrument and forming a circular lip or wedge 45, which will safely and securely engage the cocoon shaped dissector 46 as shown in FIG. 4c by closing over the circumferential recess 47 of the same, FIG. 4c. FIG. 4a shows the cocoon frame 65 having an hour glass shape with hooks 66 on the upper ends to secure the mesh gauze in position and a central threaded aperture in the base 67 to engage a manipulating screw 68.

Figure 10:
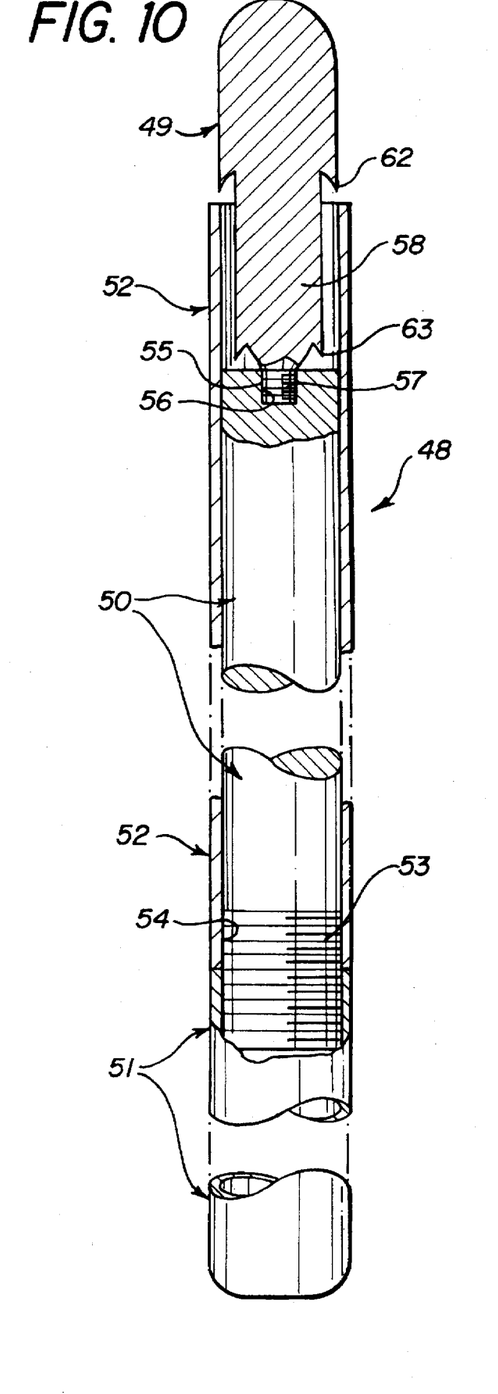
FIG. 10 is a cross sectional view of an alternate jawless embodiment of the Christoudias endodissector where the mesh tube gauze dissector is mushroom shaped and is affixed onto the main body of the instrument by screwing the dissector onto said instrument.
Figure 10A:
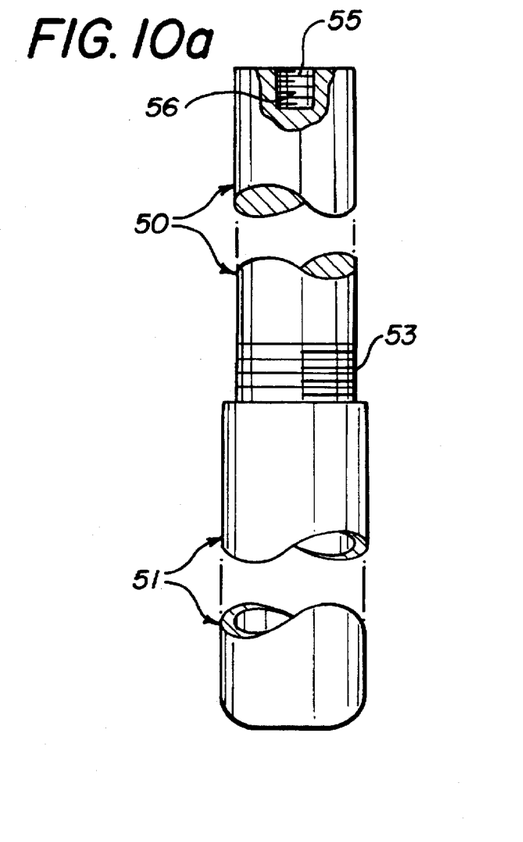
FIG. 10a shows the handle and main stem of the body of the main instrument.
Figures 11, 11A:
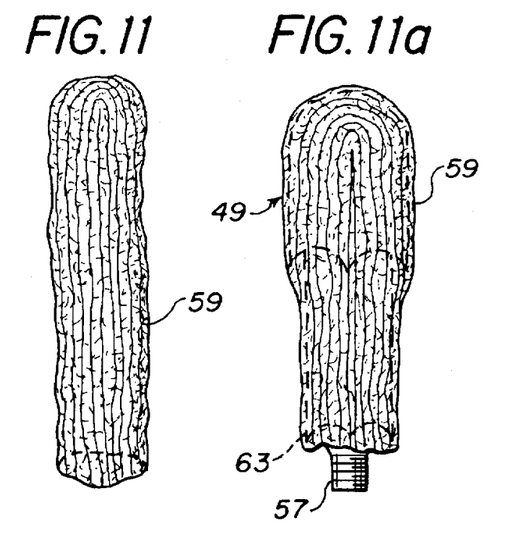
FIG. 11 shows the tubular gauze mesh.
FIG. 11a illustrates the mushroom shaped endodissector comprised of the gauze receptor and the tubular gauze.

An alternate embodiment of the "dissector transporter", 48, FIG. 10, to be used with a designated mushroom shaped dissector 49, FIG. 11a, provides means for securing the mushroom dissector 49 in a safe and efficient manner, FIG. 10.

Figure 10B:
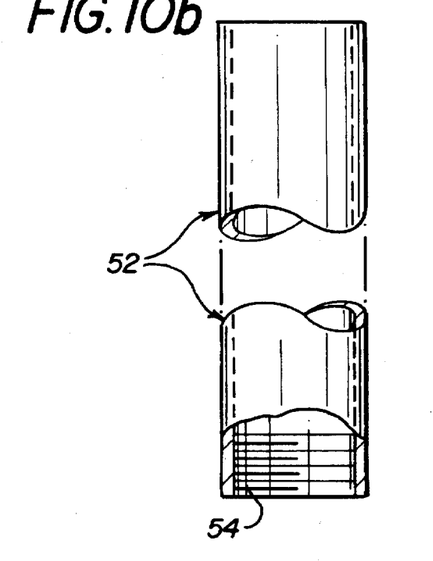
FIG. 10b shows the outer tube which protects the gauze receptor.

The "dissector transporter" 48 comprises a main stem 50 with a handle 51 on one end and the dissector 49 on the other. The handle 51 has a diameter of 2 mm greater than the main stem 50. On the main stem 50 and starting at the junction with the handle 51, there are projecting screw threads 53 to accommodate the receptor threads 54 of the outer tube 52, FIG. 10b. At the headward end of the main stem 50 and along its main axis for a distance of 5 mm there is a recess 55, 4 mm in diameter with the receptor threads 56 to accommodate the attaching screws 57 of the mushroom shaped dissector 49. The outer tube 52 is snugly attached onto the stem 50 by screwing it over the main stem's threads 53 at its junction with the handle 51.

When the outer tube 52 is snugly attached to the handle 51, the instrument is ready to accommodate the mushroom dissector 49 which will be secured by screwing its attaching screw 57 into the receptor threads 56 of the main stem 50.

The outer tube 52 projects beyond the main stem 50 so that a tubular space is formed that will house the body of the mushroom dissector 49 and ready the instrument for operation.

Figure 10C:
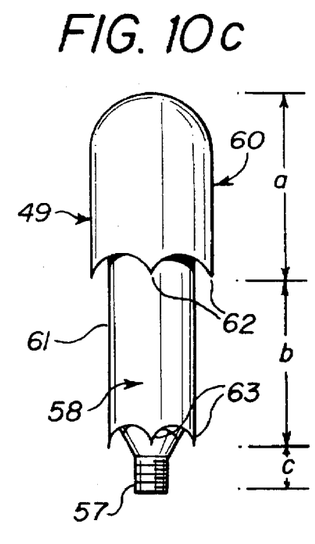
FIG. 10c shows the gauze receptor.
Figure 12:
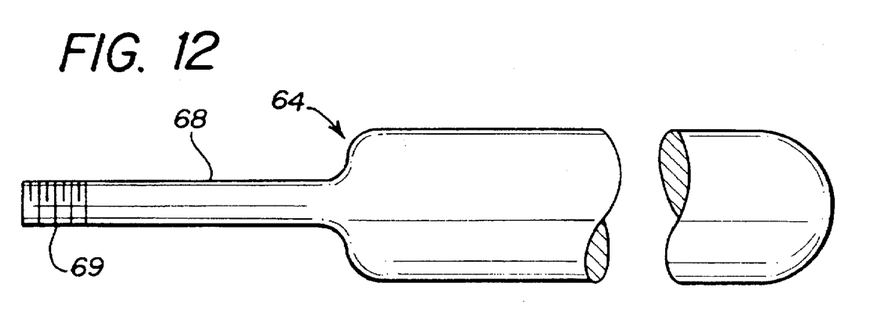
FIG. 12 shows the manipulating handle onto which the mushroom shaped gauze receptor screws in preparation for the application of the tube stretch gauze mesh thereover.
Figure 13A:
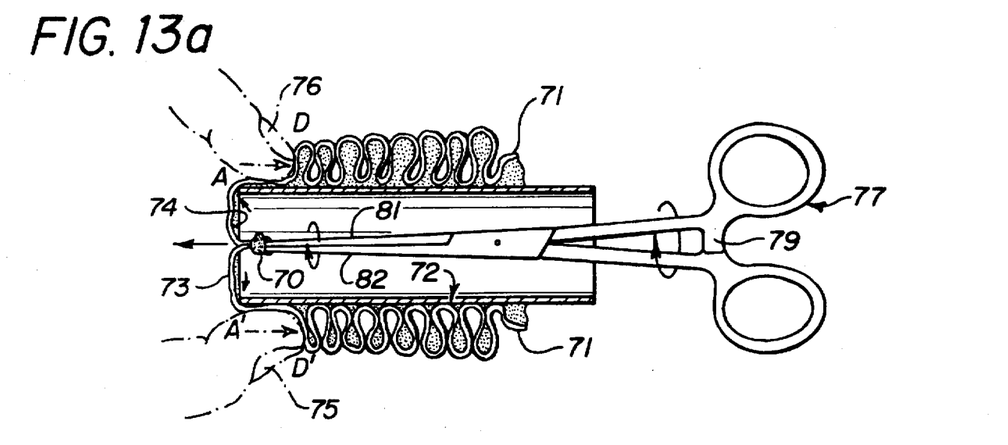
Figure 13B:
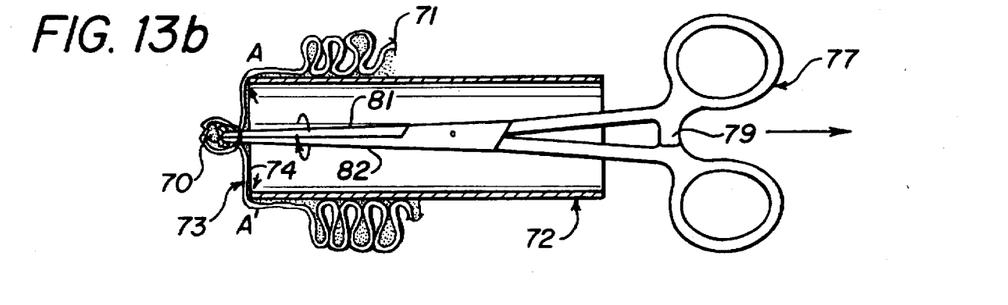
Figure 13C:
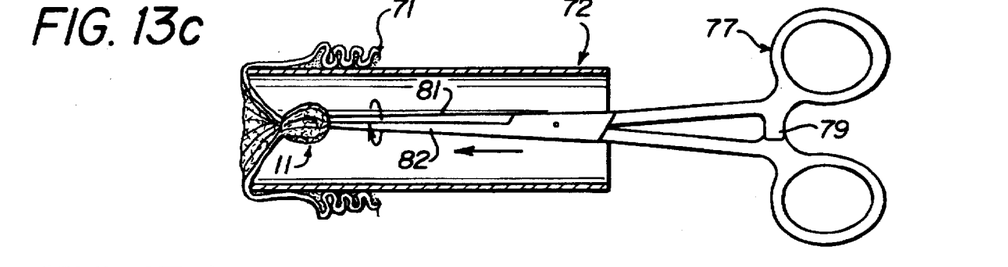
Figure 13D:
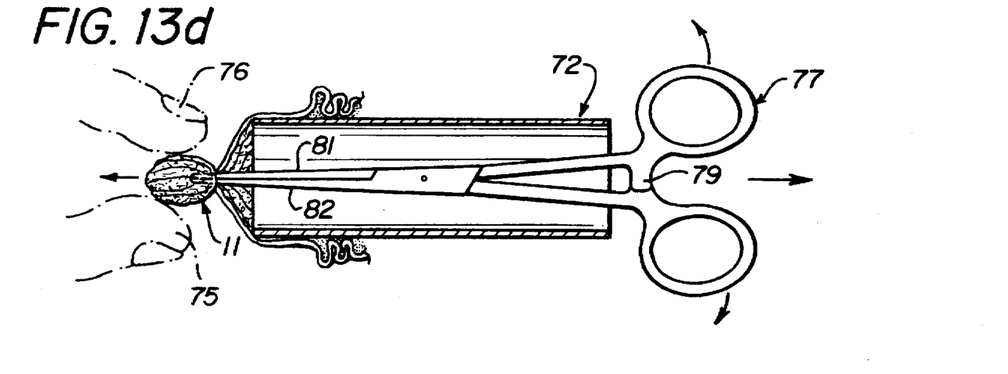
Figure 13E:
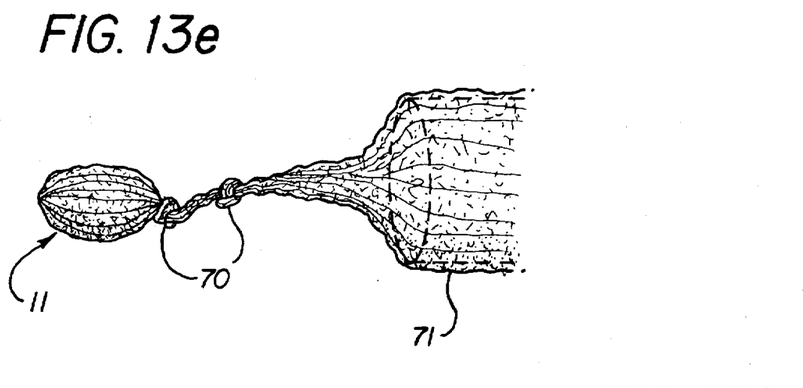
Figure 13F:
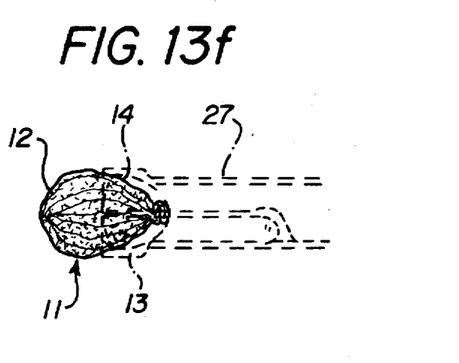

The mushroom dissector 49 comprises two elements; a frame 58, FIG. 10c and a tubular gauze 59, FIG. 11 which is mounted thereover. The frame 58 is made of plastic or metal and comprises a head 60 and body 61 and the attaching screw 57. The head 60 includes an elongated cylindrical frame surface 58 at the free end (8 mm in diameter) ending at four diametrically opposite teeth 62 projecting towards the attaching screw 57. The body 61 is attached to the head 60 at one end and has a diameter 2 mm smaller than that of the head 60 and is cylindrical in configuration. On the other end, the body 61 is centrally attached to a screw 57 which is a least 2 mm smaller in diameter, FIG. 10c. At the periphery it ends in four opposing teeth 63. The gauze 59 is a stretchable, tubular mesh gauze which can be found in the market as Surgitube® tubular gauze and has been in use for dressing digits or limbs. FIG. 12 depicts the manipulating handle 64 onto which the mushroom shaped gauze receptor 49 screws in preparation for the application of the tube stretch gauze mesh 59 thereover. The tubular gauze 59 is modified to include a radio opaque x-ray detectable fiber, such as a fiber containing barium sulfate. The method of snugly applying the gauze onto the mushroom frame will be discussed in the following paragraphs.

This invention introduces three new dissectors to be used in performance of endoscopic or conventional surgery. The basic equipment needed and the method of manufacturing these dissectors is described. The new dissectors are (a) an egg-shaped dissector 11; (b) a mushroom shaped dissector 49; and, (c) a cocoon dissector 46. The wound gauze is normally secured safely on a frame by chemical, mechanical or other physical means.

Figure 14:
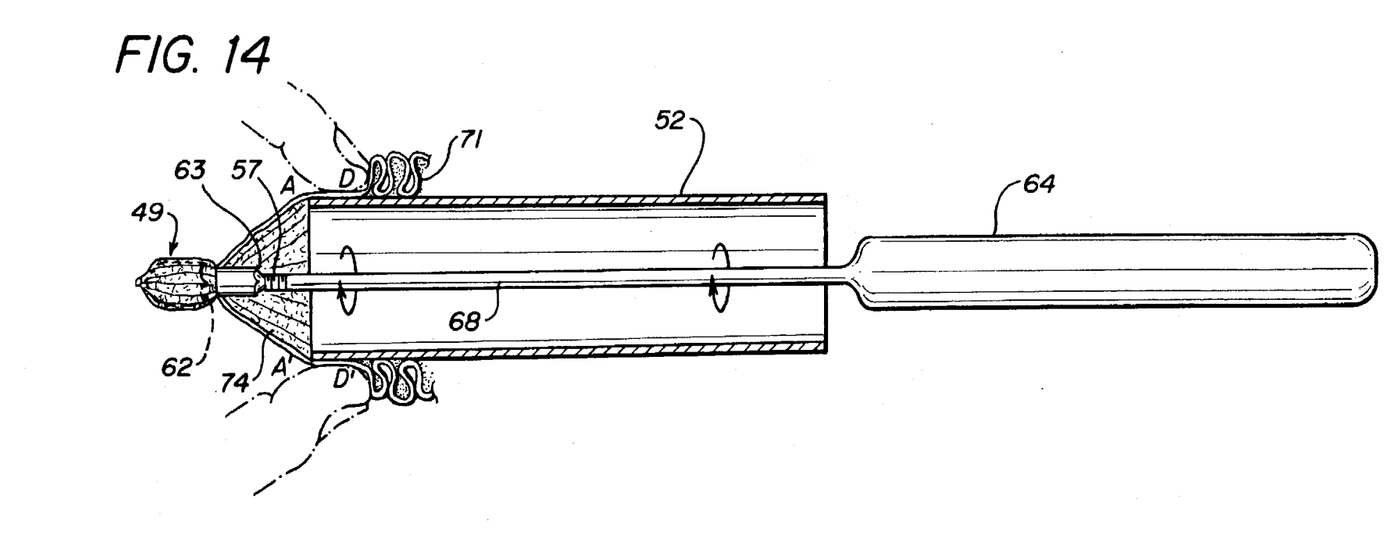
Figure 14A:
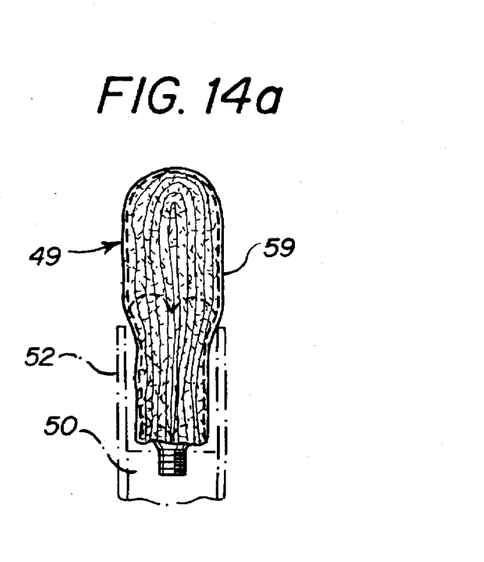
Figure 15:
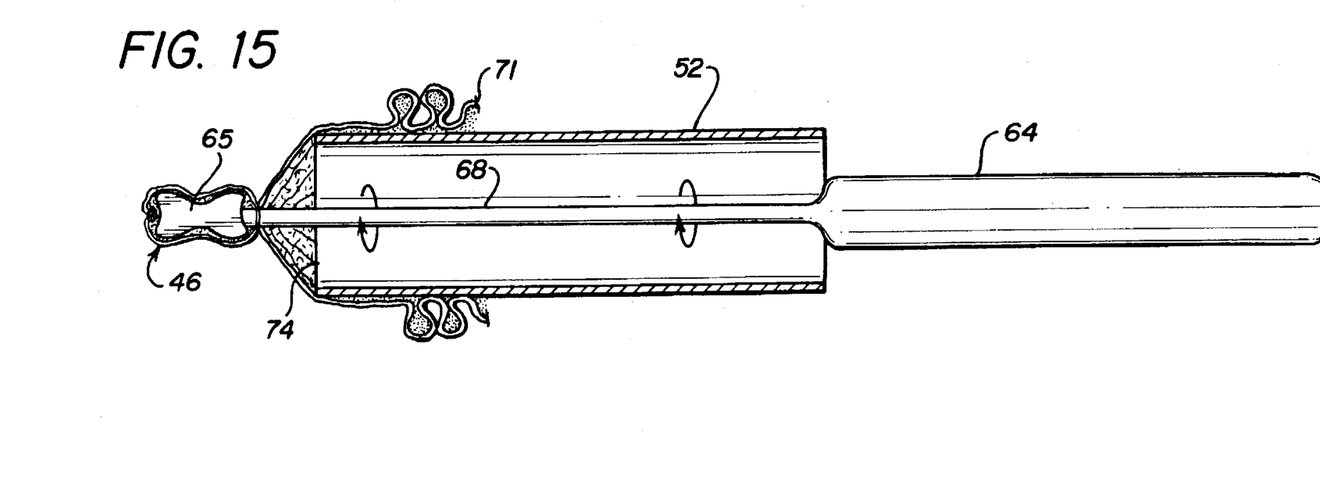
Figure 15A:
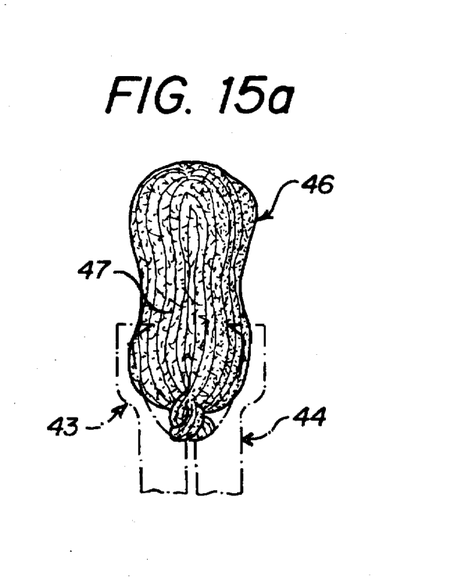

Basic Equipment for Manufacturing Dissectors, FIGS. 13, 14, 15

For a,b,c—1 Tubular, stretchable, mesh gauze 71. This modification of the D® tubular gauze that includes an x-ray detectable fiber of plastic or metal. The gauze 71 can be made of cotton, plastic or other natural or man made fiber.

For a,b,c—2 A cylindrical tubular structure 72 that will hold and feed the tubular gauze 71 to the dissector 11 mechanically or manually.

For a—3 A straight grasping instrument 77 with fine jaws 81, 82, such as a straight hemostat surgical clamp, FIG. 13a–d.

For b—4 A mushroom frame 58, FIGS. 12 and 14, and handle 64 with a stem 68 and receptor threads 69 at the end of the stem. The mushroom 49 can be made of metal or plastic, and the surface of the head is studded by a multiplicity of thorn-like teeth 62.

For c—5 A cocoon frame 65 made of metal or plastic with receptor threads 86 at one end into which a screw of a manipulating instrument can be accommodated and the manipulating instrument 68.

Description of the Drawings Demonstrating the Manufacturing of the "Dissectors"

Referring now to the drawings, the steps in the formation of the dissector 11 are shown in FIGS. 13a–f. Accordingly, a knot 70 is tied at the end of the tubular gauze 71 or the tubular gauze 71 is sutured closed at one end and the gauze 71 is guided over the cylindrical tube 72 where enough is fed to allow release of several centimeters of the covered end 73, beyond the aperture 74. The gauze release is controlled by the thumb 75 and index finger 76 of the hand holding the cylindrical tube 72. The knot or closed end is firmly grasped by the straight clamp 77 and as the tubular gauze 71 is maintained in a stretched condition by the index finger 76 and thumb 75; the clamp 77 is rotated and advanced in a direction indicated by the arrow across the threshold level of aperture 74. Step 1.

A full 360° rotation is made as the instrument knot level passes the threshold level A—A. The tubular gauze 71 snugly covers the knot 70, and as the tension on the gauze 71 and the rotational movement is maintained, Step 2, the direction of the clamp 77 with the forming dissector 11 is reversed, passing again through the threshold aperture 74 level and adding a new snugly applied layer of the gauze 71, Step 3. The back and forth motion with simultaneous rotation can be carried out as many times as desired to form a predetermined size dissector 11. Once this has been accomplished, the dissector 11 is grasped and secured with the fingers or other mechanical means, the clamp lock 79 released and the clamp 77 disengaged from the dissector 11 and removed, Step 4.

More tubular gauze 71 is then released and a knot 70 is tied by the end of the dissector 11 and another one close by, Step 5. The gauze 71 is divided between the knots 70, the dissector 11 removed, and the surgical clamp 77 grasps the knot 70 and starting with Step 1, the entire process is repeated.

The dissector 11 is sterilized with the usual process and is ready to be engaged by the dissector transport instrument 15 for use in surgery.

Now referring to FIG. 14, the mushroom frame 58 is secured on the manipulating instrument by fastening the attaching screw 57 onto the stem's receptor thread 54. The head 60 of the mushroom frame 58 is then pressed on the knot area of the tubular gauze 71 and as the gauze 71 is engaged by the plurality of the thorn-like teeth 62, the head 60 is continuously rotated with the manipulating instrument and advanced beyond the threshold aperture 74. The mushroom frame 58 is then moved back across the threshold level aperture 74 as the gauze 71 is snugly and securely applied over it one layer at a time. The last layer is just beyond the projections of the body 61 of the mushroom frame 58, the dissector 49 disengaged from the manipulating instrument, comprising the stem 68 and handle 64, and the gauze 71 cut at the level of the screw 57, allowing it to retract into the body 61 of the mushroom frame 58.

Referring now to FIG. 15 the cocoon frame is secured on the manipulating instrument comprising stem 68 and handle 64 and the same steps followed in manufacturing the cocoon dissector 46 as in producing the mushroom dissector 49 of FIG. 14.

While the invention has been explained by a detailed description of certain specific embodiments, it is understood that various modifications and substitutions can be made in any of them within the scope of the appended claims which are intended also to include equivalent of such embodiments.

What is claimed is:

1. The method of producing a dissector for an endodissector comprising the steps of:

providing a cylindrical tube having first and second open ends, and a grasping instrument;

providing a length of tubular gauze;

mounting said tubular gauze on the cylindrical tube about the first open end;

tying the tubular gauze to form a knot;

inserting the grasping instrument within the second open end and grasping the knot;

maintaining knot in a stretched condition;

rotating and advancing the grasping instrument with the knot back and forth across an aperture of the first open end to form an egg-shaped gauze configuration; and, grasping the dissector; removing the dissector from the tube and releasing the dissector from the grasping instrument.

2. The method of producing a dissector for an endodissector comprising the steps of:

providing a cylindrical tube open at a first and second end and a manipulating instrument having a frame of a predetermined configuration at one end and a handle at the outer end;

providing a length of tubular gauze; placing a portion of said tubular gauze over said tube;

insertion the frame through the tube to engage a portion of the tubular gauze; and, rotating the handle to wrap one or more layers of the gauze on the frame.

3. The method in accordance with claim 2, wherein:

the gauze is safely secured on said frame by fastening means.

4. The method in accordance with claim 2 wherein:

the frame of the dissector includes complimentary means for mechanical engagement onto a shaft of a laparoscopic instrument for safe, secure and expeditious operation.

5. The method in accordance with claim 2 wherein:

the frame has a cocoon configuration about which the gauze is wrapped.

6. The method in accordance with claim 2 wherein:

the frame has a mushroom configuration about which the gauze is wrapped.

* * * * *